US007804963B2

(12) United States Patent
Thomas et al.

(10) Patent No.: US 7,804,963 B2
(45) Date of Patent: Sep. 28, 2010

(54) METHOD AND DEVICE FOR COMPARING SIGNALS TO CONTROL TRANSDUCERS AND TRANSDUCER CONTROL SYSTEM

(75) Inventors: Jean-Philippe Thomas, Trevou Treguignec (FR); Marc Emerit, Guingamp (FR)

(73) Assignee: France Telecom SA, Paris (FR)

( * ) Notice: Subject to any disclaimer, the term of this patent is extended or adjusted under 35 U.S.C. 154(b) by 40 days.

(21) Appl. No.: 11/755,563

(22) Filed: May 30, 2007

(65) Prior Publication Data

US 2007/0286430 A1 Dec. 13, 2007

Related U.S. Application Data

(63) Continuation of application No. 10/203,856, filed on Dec. 23, 2002, now abandoned.

(51) Int. Cl.

| | |
|---|---|
| ***A61F 11/06*** | (2006.01) |
| ***H04R 29/00*** | (2006.01) |
| ***H04R 3/00*** | (2006.01) |
| ***H03G 3/00*** | (2006.01) |
| ***H04M 3/42*** | (2006.01) |
| ***H04M 1/00*** | (2006.01) |

(52) U.S. Cl. ..................... 381/71.12; 381/66; 381/71.8; 381/56; 381/104; 381/107; 381/59; 381/96; 379/202.01; 379/406.01; 379/388.02; 379/392.01

(58) Field of Classification Search ................ 381/71.2, 381/71.12, 66, 55–59, 104–107, 111, 77, 381/96, 92, 122, 71.8; 379/202.01, 406.01, 379/388.02, 392.01; 348/14.08, 14.09, 14.1, 348/14.16

See application file for complete search history.

(56) References Cited

U.S. PATENT DOCUMENTS 4,090,032 A 5/1978 Schrader
5,046,101 A 9/1991 Lovejoy
5,469,529 A 11/1995 Bimbot et al.
5,642,425 A 6/1997 Kawakami
5,729,613 A * 3/1998 Poletti ......................... 381/63
5,761,318 A 6/1998 Shimauchi et al.

(Continued)

FOREIGN PATENT DOCUMENTS

DE 19612981 A1 11/1996

(Continued)

*Primary Examiner*—Devona E Faulk
(74) *Attorney, Agent, or Firm*—Patterson Thuente Christensen Pedersen, P.A.

(57) ABSTRACT

A method of comparison between pieces of information characterizing reference values and pieces of information characterizing current values of sound-reproducing systems of a system of (n) microphones $m_i$ and (p) speakers $hp_j$ for the control of said sound-reproducing systems characterized in that: A: for each speaker $hp_j$, at least one sound signal S is sent on the speaker $hp_j$, for each microphone $m_i$, a piece of information $hp_jm_i$ is retrieved, this piece of information characterizing the sound-reproducing system comprising the speaker $hp_j$ and the microphone $m_i$, B: a reference matrix $Q_r$ is saved, this reference matrix being constituted by all the pieces of reference information $hp_jm_i$ obtained following the sending of the sound signal S, C: as soon as a comparison is to be made, the step A is run with a sound signal S' to obtain current information on a matrix Q, D: the matrices Q and $Q_r$ are compared.

30 Claims, 6 Drawing Sheets

U.S. PATENT DOCUMENTS

| | | | | |
|---|---|---|---|---|
| 5,862,233 | A * | 1/1999 | Poletti | 381/63 |
| 5,991,385 | A | 11/1999 | Dunn et al. | |
| 6,072,878 | A | 6/2000 | Moorer | |
| 6,760,451 | B1 * | 7/2004 | Craven et al. | 381/98 |

FOREIGN PATENT DOCUMENTS

| | | | |
|---|---|---|---|
| EP | 0335468 | A1 | 10/1989 |
| WO | WO 9323847 | A1 | 11/1993 |

* cited by examiner

METHOD AND DEVICE FOR COMPARING SIGNALS TO CONTROL TRANSDUCERS AND TRANSDUCER CONTROL SYSTEM

RELATED APPLICATIONS

The present application is a continuation of U.S. application Ser. No. 10/203,856 entitled "METHOD AND DEVICE FOR COMPARING SIGNALS TO CONTROL TRANSDUCERS AND TRANSDUCER CONTROL SYSTEM," filed Dec. 23, 2002, which claims priority to the PCT Application No. FR01/00457 filed Feb. 15, 2001, which claim priority to French Application No. 00 01976 filed Feb. 17, 2000, which are incorporated herein by reference.

BACKGROUND AND FIELD OF THE INVENTION

The invention relates to a method for the automatic comparison of information characterizing reference values and information characterizing current values of sound-reproducing systems of a system of microphones and speakers for the control of the sound-reproducing system.

The field of the invention is that of the automatic control of the gains, functioning and position of several microphones and several speakers in the context of a system of videoconferencing between participants located at distinct sites that are generally remote sites. The invention can also be applied to the control of microphones and speakers installed in the same room such as a theatre stage, concert hall or cinema hall. It can be used to control the spatialized sound rendition of the scene which provides concordance between visual images and sound. In the videoconferencing context, the invention makes it possible to approach a natural communications situation: when a participant changes position in a remote room during a meeting, the sound follows him in the room in which he is being listened to, with a passage, for example, from one speaker to another as he moves. The microphones and speakers are designated, without distinction, by the term transducers.

The problem is to detect the changes that occur at the transducers between their installation and the times at which the checks are made.

SUMMARY OF THE INVENTION

An object of the present invention therefore is a method of comparison between pieces of information characterizing reference values and pieces of information characterizing current values of sound-reproducing systems of a system of (n) microphones $m_i$ and (p) speakers $hp_j$ for the control of said sound-reproducing systems characterized in that:

A: for each speaker $hp_j$, at least one sound signal S is sent on the speaker $hp_j$, for each microphone $m_i$, a piece of information $hp_jm_i$ is retrieved, this piece of information characterizing the sound-reproducing system comprising the speaker $hp_j$ and the microphone $m_i$, B: a reference matrix $Q_r$ is saved, this reference matrix being constituted by all the pieces of reference information $hp_jm_i$ obtained following the sending of the sound signal S, C: as soon as a comparison is to be made, the step A is run with a sound signal S' to obtain current information on a matrix Q, D: the matrices Q and $Q_r$ are compared.

An object of the invention is also a device for comparing pieces of information characterizing reference values and pieces of information characterizing current values of sound-reproducing systems of a system of n microphones $m_i$ and p speakers $hp_j$ for the control of the sound-reproducing system, characterized in that the control system comprises means for the measurement of the pieces of information $hp_jm_i$ characterizing the sound-reproducing systems comprising a microphone $m_i$ and a speaker $hp_j$, digital processing means to compare said pieces of information $hp_jm_i$ and, connected to these digital processing means, means for saving the matrix $Q_r$ constituted by all the pieces of information $hp_jm_i$.

An object of the invention is also a system for the control of sound-reproducing systems comprising several devices such as those mentioned here above, characterized in that the devices are distributed among several rooms and in that the control system comprises a high bit-rate telecommunications network connecting said rooms and means to centralize the management of the devices.

BRIEF DESCRIPTION OF THE DRAWINGS

Other special features and advantages of the invention shall appear more clearly from the following description given by way of a non-restrictive example, with reference to the appended drawings, of which.

DETAILED DESCRIPTION OF THE DRAWINGS

Figure 1A:
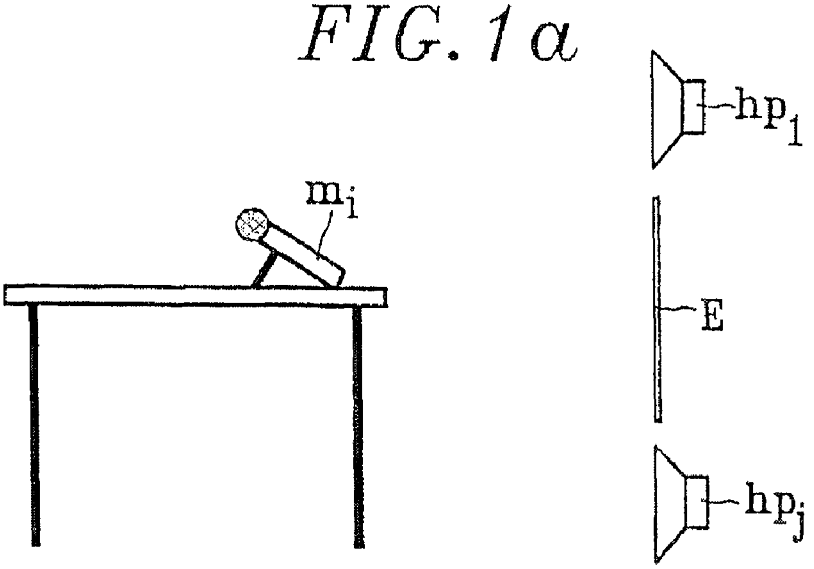
FIG. 1*a*) is a diagrammatic view of a videoconferencing room according to the invention, FIG. 1*b*) is a diagrammatic view of the direct paths between speakers and microphones, FIGS. 2*a*) and 2*b*) are views of sound-reproducing systems respectively in the case of local processing and when the processing is done in the network, FIGS. 3*a*) and 3*b*) respectively show examples of curves representing white noise and USASI noise on the one hand and pink noise and pseudo-random binary sequences on the other hand.
Figure 1B:
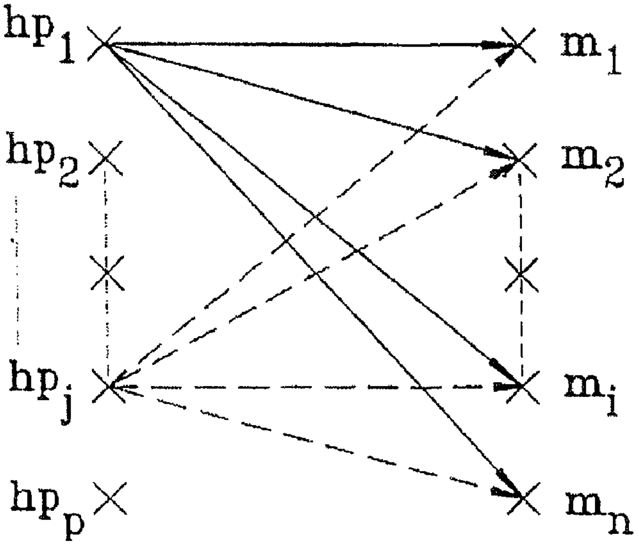

A videoconference is set up between participants distributed among several rooms, a high-bit-rate communications network such as an ATM network being used to convey visual and sound information. A videoconferencing room shown FIG. 1*a* is provided with a display screen E, several microphones $m_i$ and several speakers $hp_j$ providing for a spatialized rendition of the audiovisual scene of the remote room or rooms. The speakers may be located, without distinction, all below the screen, all on top or distributed as shown in FIG. 1*a*, or even in any other arrangement. By way of an indication, the videoconferencing room used for the invention is provided with six microphones and six speakers, the distance between microphones and speakers ranging typically from three to five meters.

The sound-reproducing systems between the microphones $m_i$ and the speakers $hp_j$ of a local processing system (shown in FIG. 2*a*), comprise the microphones $m_i$, the microphone preamplifiers $am_i$, the analog-digital converters $ADC_i$, the digital processing card, the digital-analog converters $DAN_j$, the amplifiers of the speakers $ahp_j$, the speakers $hp_j$ and the room.

Figure 2A:
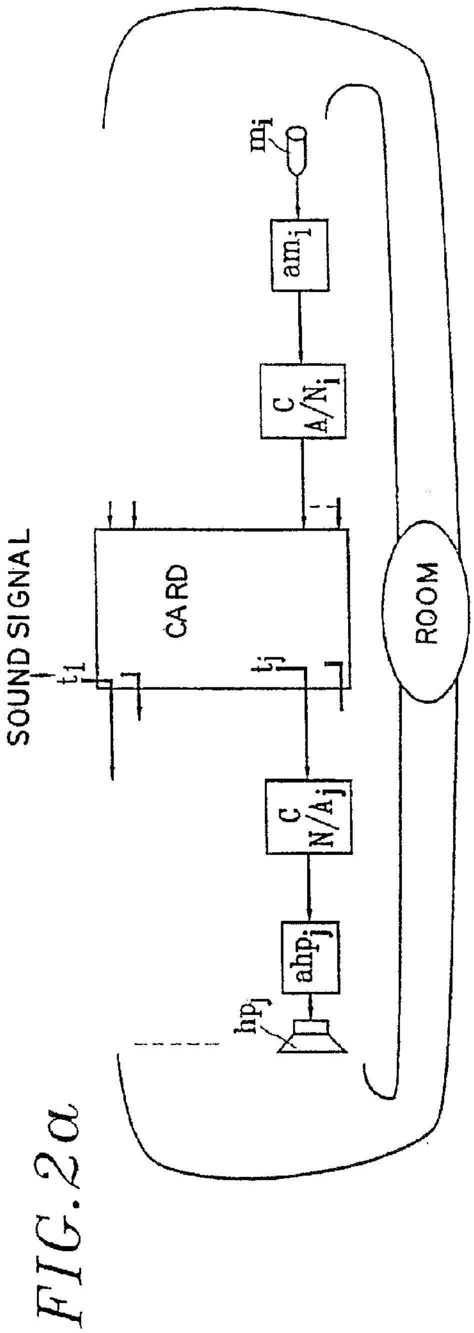
Figure 2B:
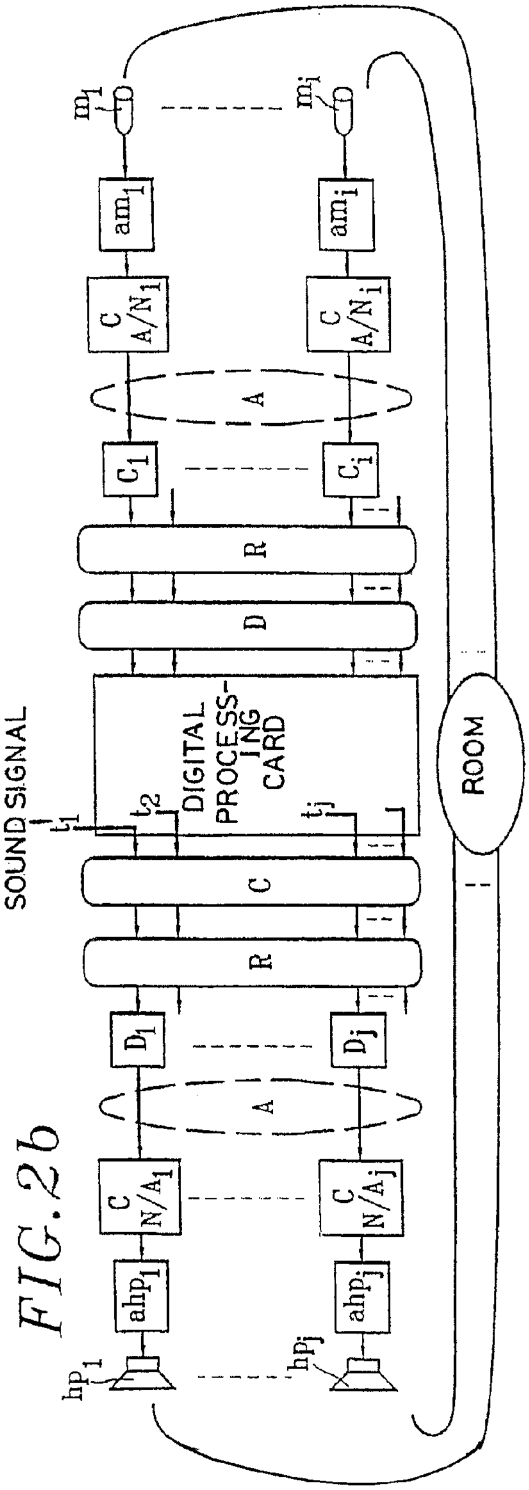

According to another embodiment, the sound-reproducing systems between the microphones $m_i$ and the speakers $hp_j$ of a remote processing system shown in FIG. 2*b*), comprise the microphones $m_i$, the microphone preamplifiers $am_i$, the analog-digital converters $ADC_i$, the encoders $C_i$, the transportation network R, the decoder D, the digital processing card, the encoder C, the transportation network R, the decoders $D_j$, the digital-analog converters $DAN_j$, the amplifiers of the speakers $ahp_j$, the speakers $hp_j$ and the room.

A routing system A obtained by a multiplexer/demultiplexer also called a switching matrix, which is commercially available, may be inserted if necessary into the sound-reproducing systems between, firstly, the analog-digital converters $ADC_i$ and the encoders $C_i$ and, secondly, the decoders $D_j$ and the analog-digital converters $ADC_j$. A remotely controllable system A of this kind makes it possible, at this level of the sound-reproducing system, to route the information characterizing a transducer from one transducer to another.

Each element of these sound-reproducing systems must be adjusted so as to provide for efficient sound transmission. During the installation of these elements, which is also known as an alignment, the gains, wirings and positions of the transducers of each room are set, and these parameters are stored in a file of a digital processing card of the signal.

To simplify the matter, the word "transducer" (speaker or microphone respectively) will designate the transducer (the speaker or microphone respectively) and the elements of the sound-reproducing system between the digital processing card and the transducer (speaker or microphone respectively).

Thereafter, when the videoconference room is used, a week or a month later for example, checks may be made on any modifications that will have occurred in these parameters in order to make the necessary corrections The transducers may have been moved and in certain cases may have become defective; the room configuration may have been changed; the amplifiers also may have been subjected to high variations over time, possibly caused by the heating of the electronic components. It may be preferred sometimes to act on the transducers in order to compensate for a defect in another element of the sound-reproducing system.

The term "sound signal" refers to a signal that can be sent by the speakers and detected by the microphones. As indicated in FIGS. 2*a*) and 2*b*), a sound signal S is sent to all the p speakers $hp_j$, one after the other at $t_1, \ldots, t_j, \ldots, t_p$, each in turn, and retrieved at the n microphones $m_i$. The reference $hp_jm_i$ is given to the piece of information characterizing the sound-reproducing system comprising the speaker $hp_j$ and the microphone $m_i$.

All these $hp_jm_i$ pieces of information constitute a matrix with a size n*p, a line of the matrix corresponding to a speaker and a column corresponding to a microphone.

The first time this matrix is constituted after the alignment, or at another preferred time, it is saved in memory: it is called the reference matrix $Q_r$, the elements $hp_jm_i$ of this matrix being reference values. Thereafter, when a check has to be made on the parameters of these transducers, these steps are reiterated with a signal S' to obtain current values $hp_jm_i$ and set up a matrix Q that is compared with the matrix $Q_r$.

In certain cases, it is simpler to choose a signal S' identical to the signal S, especially when it is sought to compare gains corresponding to the ratio between the energy of the signal sent and the energy of the signal received. In other cases, S is different from S' and the elements of the matrices $Q_r$ and Q to be compared are different in nature. By saving S and S' and by applying an adequate processing operation to the elements of Q, it is possible to deduce elements comparable to those of $Q_r$. With S being known, it is possible to choose a signal S' that enables, for example, the measurement of the impulse response or the transfer function $hp_jm_i$ between the transmission point $hp_j$ and the reception point $m_i$; given S and the characteristics of $hp_jm_i$, it is possible, from the elements $hp_jm_i$ of Q, to deduce elements comparable to those of $Q_r$ by applying an adequate processing operation (Fourier transform, . . . ).

It is also possible to set up several matrices $Q_r$ by considering several types of signals S and then set up several corresponding matrices Q. If the signal S is, for example, a white noise filtered in different octaves, it is possible to set up a matrix $Q_r$ for each octave.

In general, the elements $hp_jm_i$ are set up from signals S and S' considered in the time domain, but it is possible to base the operation on the frequency domain and set up the matrices Q and/or $Q_r$ from the spectral responses $hp_jm_i$ of the microphones $m_i$ at a frequency band sent by the speakers $hp_j$: whatever the width of the frequency band of the signals S and S' sent by the speakers $hp_j$, only a determined frequency band will be received by the microphones $m_i$ It could be a frequency band with a width of about 200 Hz, an octave band or a one-third-octave band. This frequency band will then be made in order to slide to sweep through a spectrum of 0 Hz to 1000 Hz for example.

During the alignment, the flatness of the spectrum of each transducer is verified, i.e. it is verified that all the frequencies pass through each transducer. If one of them has irregularities, the necessary corrections are made. The microphones sometimes have irregularities related to the table or room effect (to the reflections from the table or room), where the wave reflected by the table or room may be in phase opposition with the direct wave, then giving rise to black regions in the spectral response: the gain of the microphone will then be increased in the corresponding frequency band.

During subsequent checks, the spectral responses of the transducers by frequency band will be verified. The comparison between the matrices Q and $Q_r$ makes it possible, especially, to obtain a piece of information on any movement undergone by the transducers, these transducers being directional and their directivity depending on the frequency Depending on the results of the comparisons, it is also possible to make a spectral correction to the transducers in order to reduce the coupling between speakers and microphones and cause less deformation in the sound signals sent out by the participants. The exploitation of the results is sometimes more complex than it is when the operation is situated in the time domain.

The sound signals S and S' are generally recorded in the internal memory of the signal digital processing card. They may possibly be computed (generated) in this card.

Figure 3A:
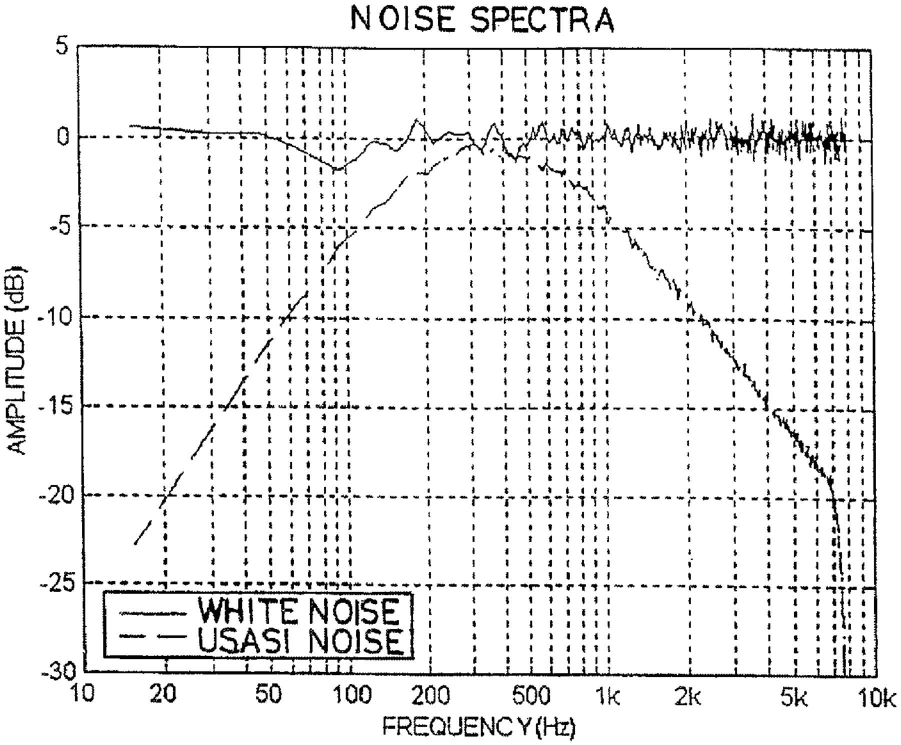
Figure 3B:
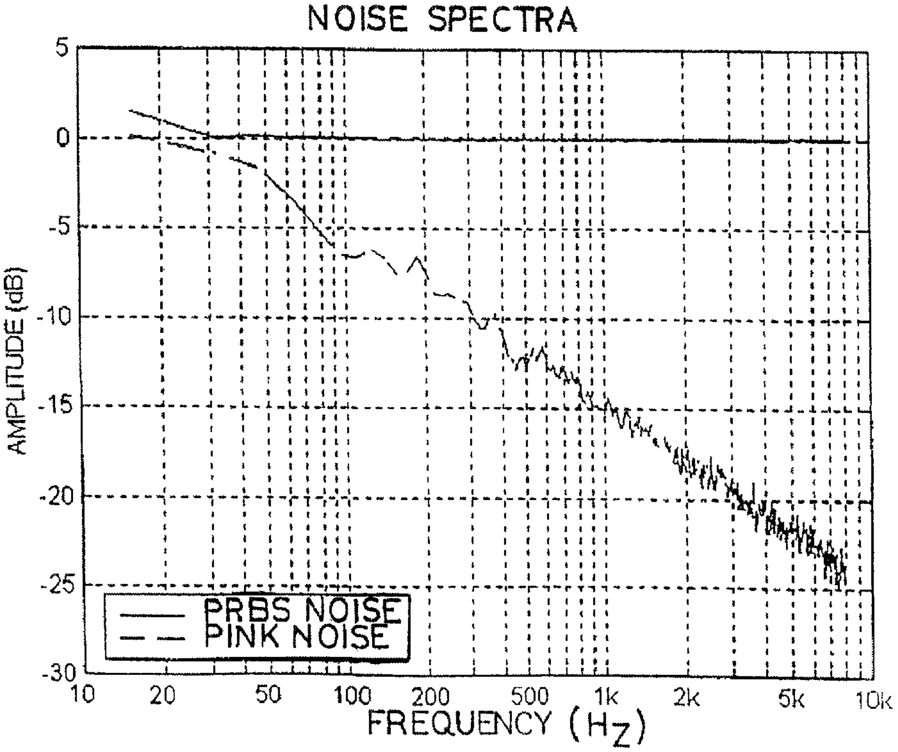

These sound signals may, for example, be a white noise, a pink noise, an USASI noise, a pseudo-random binary sequence respectively shown in FIGS. 3*a*) and 3*b*) or a sine frequency sweep, an octave-filtered noise or one-third-octave filtered noise, or again another sound signal. Unlike a random noise, a pseudo-random binary sequence is purely deterministic; it is a sequence of 1 and −1 with a length N. The characteristic feature of these sequences is that their correlation function is equal to N for 0 and to −1 for other values. This correlation function is therefore very close to a Dirac distribution.

The method according to the invention has been carried out with a pink noise sent successively to each of the speakers for one second. Between two sending operations on two consecutive speakers, there is a wait for a certain time (a period of silence) for the next sound signal to start in a state of the sound-reproducing system that is, in principle, a stable state.

The invention has been achieved with a two-second period of silence. The elements $hp_jm_i$ are determined for each $hp_j$ at the same instant t of the sound signal. If, for example, $hp_1m_1$, $hp_1m_2$, . . . , $hp_1m_n$ are determined at t=start of the sound signal+0.9 second, then $hp_2m_1$, . . . , $hp_2m_n$ will be determined at t+3 seconds, $hp_3m_1$, . . . , $hp_3m_n$ at t+6 seconds, etc.

In adding up and averaging each line and each column of the matrices $Q_r$ and Q, possibly after the processing of the elements of a matrix to obtain elements directly comparables to those of the other matrix, a mean value $HP_{jQr}$, $HP_{jQ}$ respectively for each speaker $hp_j$ is calculated by the formula:

$$1/n*\sum_{i=1}^{n} hp_jm_i,$$

and a mean value $M_{iQr}$, $M_{iQ}$ respectively for each microphone $m_i$ is calculated by the formula:

$$1/p*\sum_{j=1}^{p} hp_jm_i.$$

By computing $HP_{jQ}/HP_{jQr}$, we obtain the divergence between the speaker considered and its reference value. Similarly, by computing $M_{iQ}/M_{iQr}$, we obtain the divergence between the microphone itself and its reference value. If, for the speakers as well as the microphones, this divergence is contained in a predetermined range referenced FHP for the speakers and FM for the microphones, then no correction is applied as the difference is tolerable. A threshold of 3 dB is, for example, commonly accepted for a visioconference room. For divergence values outside the predetermined range, a corresponding divergence is applied as a corrective value to the transducer, at the signal digital processing card. As the case may be, the correction could be applied to the gain of the transducer itself. In certain cases, the correction will consist in repositioning the transducer; in other cases, it will not be possible to apply the correction because of a transducer malfunction, and the defective transducer will then be changed.

The characteristics of the pseudo-random binary sequences make them a preferred signal for the high-precision measurement of the impulse response of a system according to the invention. The use of a pseudo-random binary sequence as a sound signal sent to the speakers $hp_j$ therefore enables the measurement of the impulse responses, as a function of time $R_{ji}$, of all the microphones $m_i$. Depending on the instant at which the impulse response is considered, each impulse response $R_{ji}$ gives information on the delay, namely, the propagation time between a speaker $hp_j$ and a microphone $m_i$, the direct wave corresponding to the direct paths between a speaker $hp_j$ and microphone $m_i$, or again the room effect corresponding to the paths with one or more reflections.

Figure 4:
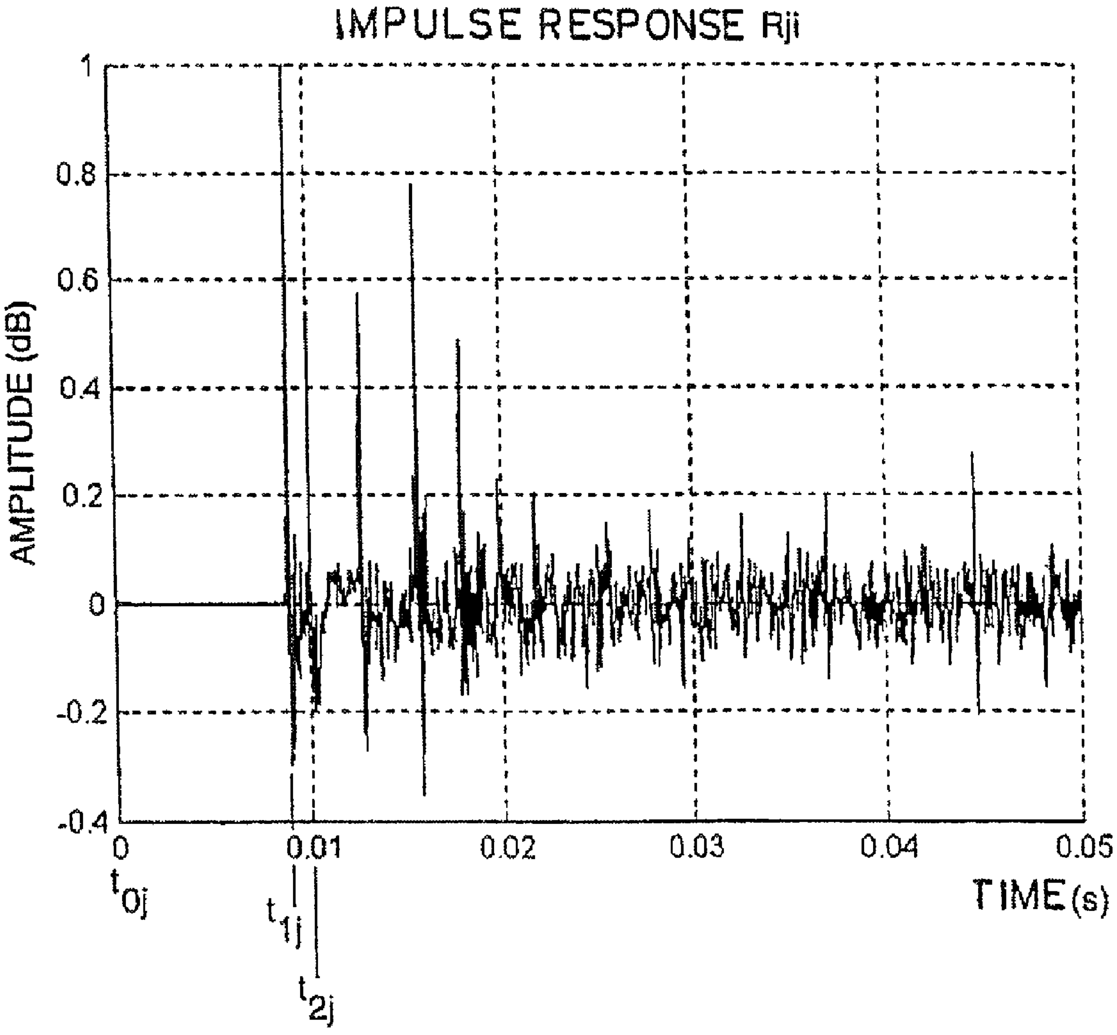
FIG. 4 shows the impulse response of a microphone following the sending, by a speaker, of a pseudo-random binary sequence.

In FIG. 4, to j denotes the instant at which the sound signal is sent from a speaker $hp_j$, $t_{1ji}$ is the instant at which the microphone $m_i$ receives the direct wave and $t_{2ji}$ is the instant at which the room effect starts for the microphone $m_i$. It is possible to measure the delays to verify the respective position of the transducers themselves. The matrix $Q_r$ is computed by measuring the delays $(hp_jm_i)_{Qr}$ for a first time. The position of the transducers is deduced from these delays by triangulation: if, for example, with the position of $hp_1$ and $hp_j$ being known, the delays $(hp_1m_1)_{Qr}$ and $(hp_jm_1)_{Qr}$ are considered, the position of the microphone $m_1$ when the reference matrix is set up is deduced from this. The same procedure is used for the other microphones. The same reasoning can be applied to determining the position of the speakers from those of the microphones. When the delays $(hp_jm_i)_Q$ of the matrix Q are subsequently computed, the transducer that has changed position will subsequently by identified by comparison with the delays of the matrix $Q_r$. In certain cases, a correction is applied to the transducer, at the signal digital processing card, to compensate for the change in position. In other cases, the correction will consist in repositioning the transducer itself.

It is thus possible to evaluate the direct wave resulting from the direct path between the speaker $hp_j$ and the microphone $m_i$. Each element $hp_jm_i$ of the matrices Q and $Q_r$ then represents the first spike of the impulse response.

When the evaluation to be made relates to the room effect due to the indirect paths between the speaker $hp_j$ and the microphone $m_i$, namely the paths of the signals that have undergone various reflections on the walls of the room, on the furniture or on any other obstacle, each element $hp_jm_i$ of the matrices Q and $Q_r$ will represent the part of the impulse response that succeeds the first spike and starts at $t_{2ji}$.

In one application of the invention, the signal-to-noise ratio of the microphones $m_i$ is evaluated by comparing the mean values of the microphones computed from the matrix $Q_r$, set up in considering a sound signal S, with the mean values of the microphones computed from the matrix Q set up in considering a signal S' of silence.

The signal S may be, especially, a white, rose or USASI noise, or a pseudo-random binary sequence. If the signal S is interspersed with silences, in practice, the signal-to-noise ratio will be measured during a phase of silence.

It is also possible to remotely process the information characterizing the signals coming from a local room, as a telecommunications or computer network connects the rooms to each other. The information processing comprises especially the measurements, computations, saving operations and corrections to be made. Remote processing can be done by a computer remotely controlling another computer, located in a local room, through the network.

It is also possible, in the local room, to deal with the case of the remote room or rooms by sending the signals S and S' through the telecommunications network and retrieving, in the local room, through the network, information characterizing the result of these signals in the remote room or rooms. The same method as described here above is used and, at the level of the signal digital processing card, coefficients are applied to the pieces of information characterizing the transmitted and retrieved signals to have a balanced system.

An echo phenomenon sometimes occurs: when a participant speaks in a room A, the corresponding sound signal is transmitted to the participants located in a room B by the speakers of this room B, the microphones of this room B taking up the signal coming from these speakers and sending them on to the room A. The speaker of the room A hears himself again with the echo. This echo can be evaluated by measuring the level of the return signal with respect to the level of the signal sent. The control parameters of the echo cancellation or transducer gain variation algorithms are then adjusted.

Figure 6:
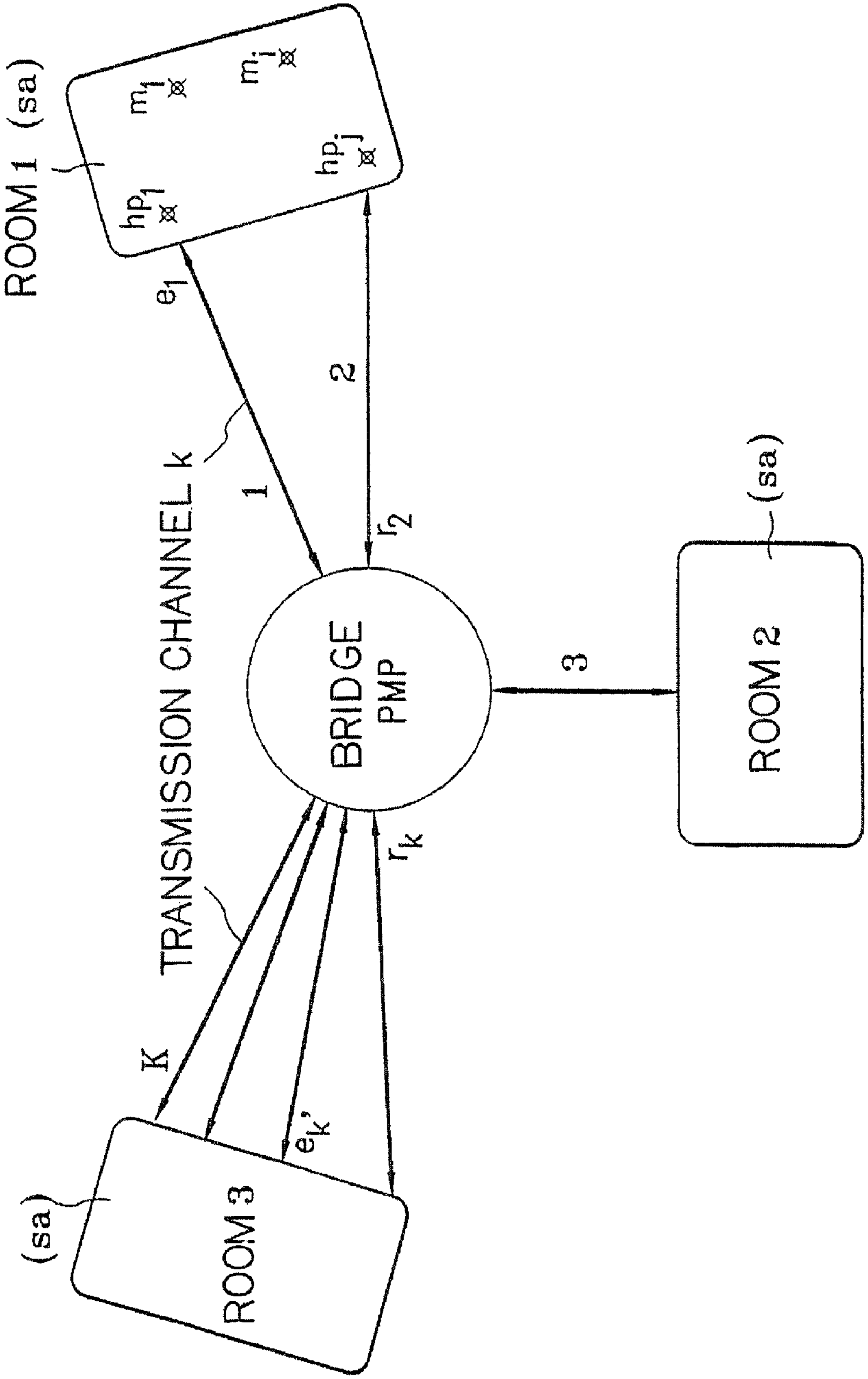
FIG. 6 is a diagrammatic view of the system of microphones and speakers distributed among several rooms connected to one another by a multipoint bridge.

It is also possible to comprehensively process the pieces of information $hp_jm_i$ in the telecommunications network, for example at the level of a multipoint bridge PMP interconnecting several remote rooms Sa, shown in FIG. 6. The signals S and S' are sent from this bridge to each room Sa through the network and retrieved at this bridge through the network.

Precise information on the equipment in each room is not always available. The elements $hp_jm_i$ are therefore no longer directly linked to the transducers but are linked to the sound-reproducing systems comprising the transmission channels k existing between the bridge PMP and each room Sa. These sound-reproducing systems result, however, for each room, from the sound-reproducing systems internal to these rooms and comprising the speakers $hp_j$ and the microphones $m_i$. Each room Sa may be connected to the bridge PMP by one or more transmission channels k. For example, two channels could be used for a room to obtain a stereophonic rendition or four could be used to obtain a quadraphonic rendition. If the transmission channels k are numbered 1 to K, then $r_k$ for example will designate the sound-reproducing system comprising a transmission channel k transmitting from the room to which it is connected to the bridge PMP and $e_k$ will designate the sound-reproducing system comprising a transmission channel k' transmitting from the bridge PMP to the room to which it is connected, where k can be equal to k'. The elements $hp_jm_i$ will then be replaced by $r_ke_{k'}$.

Figure 5:
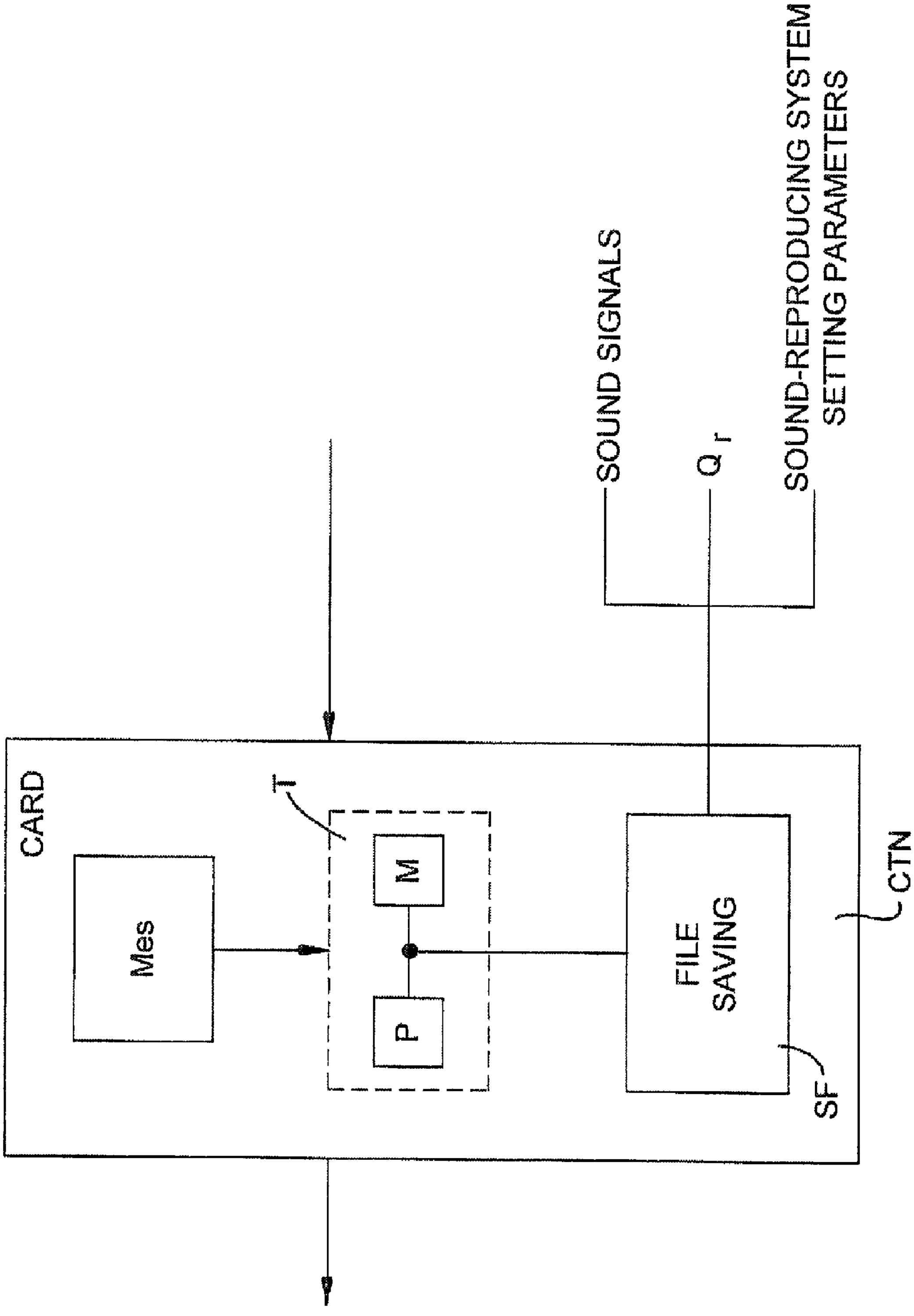
FIG. 5 is a diagrammatic view of the configuration of the signal digital processing card.

The device according to the invention comprises a signal digital processing card CTN, shown in FIG. 5. This card comprises means Mes for the measurement of the information $hp_jm_i$, processing means T and file-saving means SF such as an internal memory in which one or more sound signals are recorded. This sound signal may also be computed by the processing means T. The matrix elements $hp_jm_i$ of the matrix or matrices $Q_r$ and, possibly, one of more matrices Q are also saved in the internal memory, along with the parameters of the various elements of each of the sound-reproducing systems obtained during the setting of the room or rooms. The processing means are used to compare elements $hp_jm_i$ or combinations of these elements belonging to a same matrix Q or to several matrices. They can also be used to compute the corrections to be made to one or more elements of the sound-reproducing system and apply them. They could, for example, correct the gain of a speaker $hp_j$ and/or a microphone $m_i$. They also enable the generation of a sound signal. These processing means T will be made conventionally by means of a microprocessor P and an associated program memory M comprising a program capable of carrying out the measurements, comparisons, computations and corrections to be made.

What is claimed is:

1. A method for controlling a sound system by determining changes that occur between a current working state and a reference working state of the sound system, the method comprising:

(A) generating, for each speaker $hp_j$ of a plurality of speakers, one after another, a first predetermined sound signal as an output signal of the speaker $hp_j$, and retrieving, for each microphone $m_i$ of a plurality of microphones, the output signal generated by the microphone in response to the first predetermined sound signal generated by each speaker $hp_j$, said sound system being in the reference working state;

(B) generating and saving a reference matrix $Q_r$ of response data, said reference matrix $Q_r$ comprising a response data $hp_jm_i$ for each speaker $hp_j$ and each microphone $m_i$, each response data $hp_jm_i$ being characteristic of a sound-reproducing subsystem including the speaker $hp_j$ and the microphone $m_i$ in the reference working state, and each response data being determined by using the output signal retrieved for the microphone $m_i$ in response to the first predetermined signal output by the speaker $hp_j$;

(C) determining changes over time between the current working state and the reference working state of the sound system by:

generating a current matrix Q of response data by performing (A) and (B) with a second predetermined sound signal, said sound system being in the current working state, and comparing the current matrix Q with the reference matrix $Q_r$ by computing from the reference matrix $Q_r$ and the current matrix Q respectively, a mean value for each speaker $hp_j$ or for each microphone $m_i$, and determining if a ratio of the respective mean values is outside of a predetermined range of values; and (D) controlling the sound system by selectively adjusting the sound system in response to the changes determined in (C), when the ratio is outside of the predetermined range of values.

2. The method of claim 1, further comprising the step of: processing the current matrix Q before comparing the current matrix Q with the reference matrix $Q_r$ when the current response data is not directly comparable with the reference response data.

3. The method of claim 1, wherein further comprises: generating the reference matrix $Q_r$ of reference response data by performing (A) and (B) beforehand in the reference working state of the sound system, and generating the current matrix Q of current response data by performing (A) and (B) in the current working state, wherein the response data of at least one of the reference matrix $Q_r$ and the current matrix Q comprise a spectral response of each sound-reproducing subsystem that includes a speaker $hp_j$ and a microphone $m_i$.

4. The method of claim 3, further comprising: transmitting, in a frequency band with a predetermined width, the predetermined sound signals from the speakers $hp_j$, wherein the frequency band slides to sweep through a desired spectrum of frequencies.

5. The method of claim 1, wherein (C) further comprises: generating the reference matrix $Q_r$ of reference response data by performing (A) and (B) beforehand in the reference working state of the sound system, and generating the current matrix Q of current response data by performing (A) and (B) in the current working state, wherein the response data of at least one of the reference matrix $Q_r$ and the current matrix Q comprise an impulse response of each sound-reproducing subsystem that includes a speaker $hp_j$ and a microphone $m_i$.

6. The method of claim 1, wherein (C) further comprises: generating the reference matrix $Q_r$ of reference response data by performing (A) and (B) beforehand in the reference working state of the sound system, and generating the current matrix Q of current response data by performing (A) and (B) in the current working state, wherein the response data of at least one of the reference matrix $Q_r$ and the current matrix Q comprise a transfer function of each sound-reproducing subsystem that includes a speaker $hp_j$ and a microphone $m_i$.

7. The method of claim 1, wherein (C) further comprises: generating the reference matrix $Q_r$ of reference response data by performing (A) and (B) beforehand in the reference working state of the sound system, and generating the current matrix Q of current response data by performing (A) and (B) in the current working state, wherein the response data of at least one or the reference matrix $Q_r$ and the current matrix Q comprise a gain between the microphones $m_i$ and the speakers hp following the predetermined sound signals sent from the speakers $hp_j$.

8. The method of claim 1, wherein the plurality of microphones comprises n number of microphones, and wherein computing a mean value for each speaker $hp_j$ and determining if a ratio of the respective mean values is outside of a predetermined range of values comprises:

from the matrices Q and $Q_r$, respectively, computing the mean value corresponding to each speaker $hp_j$, respectively referenced as $HP_{jQ}$ and $HP_{jQr}$, by $$1/n*\sum_{i=1}^{n} hp_j m_i,$$

and wherein controlling the sound system comprises:

correcting a divergence corresponding to $Hp_{jQr}/HP_{jQ}$ in each sound-reproducing subsystem comprising a speaker $hp_j$ when the value $Hp_{jQ}/HP_{jQr}$ is outside a predetermined speaker range FHP.

9. The method of claim 8, further comprising correcting a gain of the speaker $hp_j$ for each sound-reproducing subsystem comprising a speaker $hp_j$.

10. The method of claim 8, wherein (C) further comprises:

generating the reference matrix $Q_r$ of reference response data by performing (A) and (B) beforehand in the reference working state of the sound system, and generating the current matrix Q of current response data by performing (A) and (B) in the current working state, wherein the respective response data of the matrices $Q_r$ and Q comprise impulse responses of each sound-reproducing subsystem including a speaker $hp_j$ and a microphone $m_i$, and wherein the response data correspond to the sound signals received by the microphone $m_i$ from a direct path between the speaker $hp_j$ and the microphone $m_i$.

11. The method of claim 8, wherein (C) further comprises:

generating the reference matrix $Q_r$ of reference response data by performing (A) and (B) beforehand in the reference working state of the sound system, and generating the current matrix Q of current response data by performing (A) and (B) in the current working state, wherein the respective response data of matrices $Q_r$ and Q comprise impulse responses of each sound-reproducing subsystem including a speaker $hp_j$ and a microphone $m_i$, and wherein the response data correspond to the sound signals received by the microphone $m_i$ from paths with one or more reflections between the speaker $hp_j$ and the microphone $m_i$.

12. The method of claim 1, wherein the plurality of speakers comprises p number of speakers, and wherein computing a mean value for each microphone $m_i$, and determining if a ratio of the respective mean values is outside of a predetermined range of values comprises:

from the matrices Q and $Q_r$, respectively, computing the mean value corresponding to each microphone $m_i$, respectively referenced $M_{iQ}$ and $M_{iQr}$, by $$1/p*\sum_{j=1}^{p} hp_j m_i,$$

and wherein controlling the sound system comprises:

correcting a divergence corresponding to $M_{iQr}/M_{iQ}$ in each sound-reproducing subsystem comprising a microphone $m_i$ when the value of $M_{iQ}/M_{jQr}$ is outside a predetermined microphone range FM.

13. The method of claim 12, further comprising correcting a gain of the microphone $m_i$ for each sound-reproducing subsystem comprising a microphone $m_i$.

14. The method of claim 1, wherein (C) further comprises:

generating the reference matrix $Q_r$ of reference response data by performing (A) and (B) beforehand in the reference working state of the sound system, and generating the current matrix Q of current response data by performing (A) and (B) in the current working state, wherein the response data of the matrices $Q_r$ and Q represent delays between sending the predetermined sound signal from each speaker $hp_j$ and reception of the sound signal by each microphone $m_i$.

15. The method of claim 1, wherein the plurality of speakers comprises p number of speakers, and wherein computing a mean value for each microphone $m_i$, and determining if a ratio of the respective mean values is outside of a predetermined range of values comprises:

determining, from said matrices Q and $Q_r$, respectively, the mean value corresponding to each microphone $m_i$, referenced respectively $M_{iQ}$ and $M_{iQr}$, by $$1/p*\sum_{j=1}^{p} hp_j m_i,$$

to obtain a signal-to-noise ratio $M_{iQr}/M_{iQ}$ of the microphones, wherein the second predetermined sound signal used to constitute the current matrix Q is a silence signal.

16. The method of claim 1, further comprising:

remotely processing the response data of at least one of the matrices Q and $Q_r$ through a telecommunications or computer network.

17. The method of claim 1, further comprising:

processing the response data in a local room, wherein the response data corresponds to predetermined sound signals constituting at least one of the matrices $Q_r$ and Q and originating from a remote room connected to the local room through a telecommunications network.

18. The method of claim 1, wherein (C) further comprises:

generating the reference matrix $Q_r$ of reference response data by performing (A) and (B) beforehand in the reference working state of the sound system, and generating the current matrix Q of current response data by performing (A) and (B) in the current working state, wherein the response data of matrices $Q_r$ and Q represent an echo, and wherein the predetermined sound signals used to constitute the matrices originate from a remote room connected to a local room through a telecommunications network.

19. The method of claim 1, applied to a plurality of remote rooms, each remote room respectively equipped with a sound system connected to a multipoint bridge of a telecommunications network by at least one transmission channel, and wherein for each remote room the method further comprises:

transmitting said first predetermined sound signal, generated at (A) to be emitted by each speaker $hp_j$, to the remote room from said multipoint bridge through a first one of the at least one transmission channels of the telecommunications network; and transmitting the output signal, retrieved at (A) for each microphone $m_i$, from the remote room to the multipoint bridge through a second one of the at least one transmission channels of the telecommunications network;

wherein (B) and (C) are performed in the multipoint bridge, each response data of the reference matrix $Q_r$ and of the current matrix Q, for the respective remote room considered, being characteristic of a sound-reproducing subsystem that includes the first one of the at least one transmission channels from the respective remote room considered to the multipoint bridge, and the second one of the at least one transmission channels from the multipoint bridge to the respective remote room considered.

20. The method of claim 19, at least one of the predetermined sound signal used to generate matrix $Q_r$ and the second predetermined sound signal used to generate matrix Q is selected from the group consisting of: a white noise, a pink noise, a USASI noise, and a pseudo-random binary sequence.

21. The method of claim 19, wherein the second predetermined sound signal used to constitute the current matrix Q is the same as the first predetermined sound signal used to obtain the reference matrix $Q_r$.

22. The method of claim 1, wherein at least one of the first predetermined sound signal used to generate matrix $Q_r$ and the second predetermined sound signal used to generate matrix Q is selected from the group consisting of: a white noise, a pink noise, a USASI noise, and a pseudo-random binary sequence.

23. The method of claim 1, wherein the second predetermined sound signal used to constitute the current matrix Q is the same as the first predetermined sound signal used to obtain the reference matrix $Q_r$.

24. A device for controlling a sound system by determining changes that occur between a current working state and a reference working state of the sound system, the sound system comprising a plurality of microphones and a plurality of speakers, the device comprising:

means for generating, for each speaker $hp_j$ of the plurality of speakers, one after another, a first predetermined sound signal as an output signal of the speaker $hp_j$ when the sound system is in the reference working state, and for generating a second predetermined sound signal as an output signal of the speaker $hp_j$ when the sound system is in the current working state;

means for retrieving, for each microphone $m_i$ of the plurality of microphones, the output signal generated by the microphone $m_i$ in response to either the first or second predetermined sound signal generated by each speaker $hp_j$;

means for generating and saving a reference matrix Qr of response data, said reference matrix $Q_r$ comprising a response data $hp_jm_i$ for each speaker $hp_j$ and each microphone $m_i$, the response data being characteristic of a first sound-reproducing subsystem including the speaker $hp_j$ and the microphone $m_i$ in the reference working state, and the response data being determined by using the output signal retrieved for the microphone $m_i$ in response to the first predetermined signal output by the speaker $hp_j$, and for generating and saving a current matrix Q of response data, said current matrix Q comprising a response data $hp_jm_i$ for each speaker $hp_j$ and each microphone $m_i$, the response data being characteristic of a second sound-reproducing subsystem including the speaker $hp_j$ and the microphone $m_i$ in the current working state, and the response data being determined by using the output signal retrieved for the microphone $m_i$ in response to the second predetermined signal output by the speaker $hp_j$;

means for comparing the current matrix Q generated for the current working state of the sound system with the reference matrix $Q_r$ generated beforehand for the reference working state of the sound system to determine changes over time between the current working state and the reference working state, by computing from the reference matrix $Q_r$ and the current matrix Q respectively, a mean value for each speaker $hp_j$ or for each microphone $m_i$, and determining if a ratio of the respective mean values is outside a predetermined range of values; and means for controlling the sound system by selectively adjusting the sound system in response to a change determined as a result of comparing the current matrix Q and the reference matrix $Q_r$ when the ratio is outside of the predetermined range of values.

25. The device of claim 24, wherein the first predetermined sound signal and the second predetermined sound signal are selected from the group consisting of: a white noise, a pink noise, an USASI noise, and a pseudo-random binary sequence.

26. The device of claim 24, further comprising means to correct properties of a speaker $hp_j$ and a microphone $m_i$ of a subsystem comprising the speaker $hp_j$ and the microphone $m_i$ according to a difference determined between the current working state and the reference working state.

27. The device of claim 26, wherein a gain of the speaker $hp_j$ is corrected in the subsystem comprising the speaker $hp_j$.

28. The device of claim 26, wherein a gain of the microphone $m_i$ is corrected in the subsystem comprising the microphone $m_i$.

29. A control system for sound systems, comprising a plurality of devices according to claim 24, wherein the devices are distributed among a plurality of rooms, and wherein the control system comprises:

a high bit-rate telecommunications network connecting the plurality of rooms; and means to centralize management of the devices.

30. The control system of claim 29, wherein the means to centralize management of the devices are located at a point of the telecommunications network connecting the plurality of rooms, each room being connected to the point of the telecommunications network by at least one transmission channels, the control system comprising means to selectively correct properties of a speaker $hp_j$ and a microphone $m_i$ of a sound-reproducing subsystem of a sound system in a room, the sound-reproducing subsystem including at least one transmission channel connecting the room to the point of the telecommunications network.

* * * * *

UNITED STATES PATENT AND TRADEMARK OFFICE

CERTIFICATE OF CORRECTION

PATENT NO. : 7,804,963 B2
APPLICATION NO. : 11/755563
DATED : September 28, 2010
INVENTOR(S) : Thomas et al.

It is certified that error appears in the above-identified patent and that said Letters Patent is hereby corrected as shown below:

Title Page

Field 63:
After "now abandoned" insert --filed as application No. PCT/FR01/00457 on February 15, 2001--

Insert Field (30):
--(30) Foreign Application Priority Data
Feb. 17, 2000 (FR) 00/01976--

Signed and Sealed this
Eighth Day of May, 2012

David J. Kappos
*Director of the United States Patent and Trademark Office*